US007083932B1

(12) United States Patent
Parmentier et al.

(10) Patent No.: US 7,083,932 B1
(45) Date of Patent: Aug. 1, 2006

(54) NUCLEIC ACID MOLECULES ENCODING PEPTIDES HAVING PRONOCICEPTIVE PROPERTIES

(75) Inventors: Marc Parmentier, Linkebeek (BE); Gilbert Vassart, Brussels (BE); Jean-Claude Meunier, Rebigue (FR); Catherine Mollereau, Castanet (FR)

(73) Assignee: Euroscreen, s.a., Gosselies (BE)

( * ) Notice: Subject to any disclaimer, the term of this patent is extended or adjusted under 35 U.S.C. 154(b) by 0 days.

(21) Appl. No.: 09/011,797

(22) PCT Filed: Aug. 14, 1996

(86) PCT No.: PCT/BE96/00087

§ 371 (c)(1),
(2), (4) Date: Jul. 23, 1997

(87) PCT Pub. No.: WO97/07208

PCT Pub. Date: Feb. 27, 1997

Related U.S. Application Data

(60) Provisional application No. 60/002,368, filed on Aug. 15, 1995.

(51) Int. Cl.
*G01N 33/566* (2006.01)
*C12N 15/00* (2006.01)
*C12N 15/12* (2006.01)
*C12N 15/63* (2006.01)
*C07K 14/00* (2006.01)

(52) U.S. Cl. .................. 435/7.2; 435/69.1; 435/320.1; 435/325; 530/350; 530/326; 530/328; 536/23.5

(58) Field of Classification Search ............... 530/350, 530/326, 328, 23.5; 435/69.1, 320.1, 325, 435/7.2
See application file for complete search history.

(56) References Cited

U.S. PATENT DOCUMENTS 5,837,809 A * 11/1998 Grandy et al. .............. 530/326

FOREIGN PATENT DOCUMENTS

| WO | WO 9202554 | * | 2/1992 |
| WO | WO 93/21309 | | 10/1993 |
| WO | WO 94/01548 | | 1/1994 |
| WO | WO 95/12616 | | 5/1995 |

OTHER PUBLICATIONS

Mikayama T. Molecular cloning and functional expression of a cDNA encoding glycosylation-inhibiting factor. Proc. Natl. Acad. Sci. USA vol. 90, pp. 10056-10060, 1993.*
Voet et al. Biochemistry. 1990. John Wiley & Sons, Inc.. pp. 126-128 and 228-234.*
Stratagene Catalogue 1991, p. 66.*
Voet et al. Biochemistry. 1990, John Wiley & Sons, inc. pp. 126-128 and 228-234.*
Catherine Mollereau et al., *ORL1, a novel member of the opioid receptor family. Cloning functional expression and localization.* FEBS Letters, vol. 341, 1994, pp. 33-38.
Jean-Claude Meunier et al., *Isolation and structure of the endogenous agonist of opioid receptor-like $ORL_1$ receptor,* Letters to Nature, vol. 377, Oct. 12, 1995, pp. 532-535.
Yumiko Saito et al., *N23K, A Gene Transiently Up-Regulated During Neural Differentiation, Encodes a Precursor Protein for a Newly Identified Neuropeptide Nociceptin,* Biochemical and Biophysical Research Communications, vol. 217, No. 2, Dec. 14, 1995, pp. 539-545.
Christopher W. Vaughan et al., *Increase by the $ORL_1$ receptor* (opioid receptor-like$_1$) *ligand, nociceptin, of inwardly rectifying K conductance in dorsal raphe nucleus neurones,* British Journal of Pharmacology, vol. 117, 1996, pp. 1609-1611.
Shengwen Zhang et al., *Identification of Dynorphins as Endogenous Ligands for an Opioid Receptor-like Orphan Receptor,* The Journal of Biological Chemistry, vol. 270, No. 39, Sep. 29, 1995, pp. 22772-22776.
Rainer K. Reinscheid et al., *Orphanin FQ: A Neuropeptide That Activates an Opioidlike G Protein-Coupled Receptor,* SCIENCE, vol. 270, Nov. 3, 1995, pp. 792-794.

* cited by examiner

*Primary Examiner*—Joseph Murphy
(74) *Attorney, Agent, or Firm*—Kathleen M. Williams; Palmer & Dodge LLP (57) ABSTRACT

The present invention is related to nucleic acid molecules, the peptides encoded by said nucleic acid moleucles and the inhibitors diereacted against said nucleic acid molecules or said peptides. The present invention concerns also the pharmaceutical composition, the diagnostic and/or dosage device comprising said products and methods for identifying the inhibitors according to the invention.

5 Claims, 11 Drawing Sheets

```
                        1           5            10          15
ORL₁-HpDPep  :   F  |G  G  F|  T  G  A  R  K  S  A  R  |K|  L  A  |N  Q|

DYNORPHIN A  :   Y  |G  G  F|  L  R  R  I  R  P  K  L  |K|  W  D  |N  Q|
                    ←──────→ ←──────────────────────────────────→
                    "message"        " address"
```

LOCOMOTOR ACTIVITY (crossed beams)

US 7,083,932 B1

NUCLEIC ACID MOLECULES ENCODING PEPTIDES HAVING PRONOCICEPTIVE PROPERTIES

This is a §371 application of PCT/BE96/00087. This application claims the benefit of U.S. Provisional Patent Application No. 60/002,368 filed on Aug. 15, 1995.

FIELD OF THE INVENTION

The present invention is related to nucleic acid molecules, the peptides encoded by said nucleic acid molecules and the inhibitors directed against said nucleic acid molecules or said peptides.

The present invention concerns also the pharmaceutical composition, the diagnostic and/or dosage device comprising said products and methods for identifying the inhibitors according to the invention.

Various opioid receptors were described and used for the screening of improved drugs.

The present invention is related to a new nucleic acid, especially a nucleic acid encoding peptides which have less than 70% homology with the peptides with are known to be ligands of the opioid receptors, said peptides having pronociceptive properties.

The inhibitors of said nucleic acid molecules or encoded peptides could be used as new types of drugs in the control of various behaviours or functions such as neuroendocrine secretion, stress, learning and memory, attention and emotions, homeostasis, sensory perception, motricity (locomotion), anxiety, instinctive behaviours, hyperalgesia or hypoalgesia, . . . .

SUMMARY OF THE INVENTION

The present invention is related to a nucleic acid molecule which corresponds to at least 70%, preferably at least 90%, of the SEQ ID NO. 1 or its complementary strand.

Preferably, the nucleic acid molecule according to the invention is an isolated nucleic acid molecule comprising at least the sequence SEQ ID NO 1, or its complementary strand or a portion thereof.

It is meant by a "nucleic acid molecule", a RNA or a DNA such as a cDNA or a genomic DNA.

It is meant by a "portion of an isolated nucleic acid molecule", any kind of nucleic acid molecule which is specific of SEQ ID NO. 1 such as a probe or one or several primer(s) which could be used in order to identify and reconstitute said specific isolated nucleic acid molecule, for instance by genetic amplification (PCR, LCR, CPR, . . . ) or by specific probe hybridization. Therefore, a portion of said nucleic acid molecule is any portion of said nucleic acid molecule having more than 15 nucleotides and which is specific of SEQ ID NO. 1.

The present invention concerns also any peptide encoded by the nucleic acid molecule according to the invention. Therefore, said peptide may be a precursor of an active peptide which means a peptide which should be cleaved at a specific side in order to be active. An example of said peptide is the prepronociceptine described hereafter which is cleaved into two active heptadecapeptides according to the invention.

A preferred embodiment of the present invention concerns the peptide which has the amino sequence of SEQ ID NO. 2: Phe-Gly-Gly-Phe-Thr-Gly-Ala-Arg-Lys-Ser-Ala-Arg-Lys-Leu-Ala-Asn-Gln or agonists thereof, said peptide being a ligand of the $ORL_1$ receptor, preferably a ligand of the mammal $ORL_1$ receptor, more specifically a ligand of the human $ORL_1$ receptor.

Another embodiment of the present invention concerns the peptide which has the amino sequence of SEQ ID NO. 3: Phe-Ser-Glu-Phe-Met-Arg-Gln-Tyr-Leu-Val-Leu-Ser-Met-Gln-Ser-Ser-Gln, or agonists.

A further embodiment of the present invention concerns a peptide which has the amino sequence of SEQ ID NO. 4: Thr-Leu-His-Gln-Asn-Gly-Asn-Val, or agonists.

An agonist according to the invention, may be a molecule which mimics the peptide interaction with its receptor(s). Such may be analogs or fragments of the peptide according to the invention, or antibodies directed against the ligands binding side epitopes of the peptide receptors, or anti-idiotypic antibodies directed against particular antibodies which bind to receptor-interacting specific portions of the peptide according to the invention.

Said antibodies can be raised to the peptide fragments and analogs, both in their naturally occurring forms, and in their recombinant forms. Additionally, antibodies can be raised to the peptide either in its active forms or in its inactive forms.

Another aspect of the present invention concerns the inhibitor directed against the nucleic acid molecule or the peptide according to the invention. An inhibitor is any kind of molecule which is able to avoid translation of the nucleic acid molecule according to the invention or avoid or reduce the interaction of the peptide or a portion of said peptide to its receptor.

Advantageously, the inhibitor according to the invention is a polyclonal or a monoclonal antibody or a portion thereof, especially the epitope portion of an antibody such as the portions Fab', Fab, $F(ab')_2$, of said antibody.

According to another embodiment of the present invention, said inhibitor is any molecule which may interact with the nucleic acid molecule according to the invention and prevent its expression in a cell of an animal, such as a mammalian, preferably a human.

Advantageously, said inhibitor is an antisense oligonucleotide which has a sequence capable of specifically binding to the nucleic acid molecule according to the invention so as to prevent its expression (its transcription and/or its translation).

Preferably, said inhibitor comprises chemical analogs of nucleotides having advantageously sequences which differ from one another at predefined positions. Said oligonucleotides could be coupled to a substance such as a rybozyme which inactivates the nucleic acid according to the invention.

Said inhibitor could also be an antagonist to the receptor of the peptide according to the invention. An antagonist is a ligand of said receptor which blocks the interaction of the peptide to its receptor.

The present invention is also related to a vector comprising the nucleic acid molecule according to the invention.

Another aspect of the present invention is related to a pharmaceutical composition comprising an element chosen among the group consisting of the nucleic acid molecule, the peptide, the inhibitor or the vector according to the invention and a pharmaceutically acceptable carrier.

A pharmaceutical carrier can be any compatible non-toxic substance suitable for delivering the composition of the invention to a patient.

Preferably, said pharmaceutical composition comprises also an amount of a substance effective to reduce the expression and/or the "effects" resulting from the expression of the peptide or the nucleic acid molecule according to the invention.

The dosage of the active ingredients in the pharmaceutical composition may vary according to the pharmaceutically acceptable carrier used, the patient treated and the side effects of said active ingredients.

The pharmaceutical composition according to the invention is advantageously used for the treatment and/or the prevention of a disease related to the following functions and/or behaviours: hyperalgesia, hypoalgesia, neuroendocrine secretion, stress, anxiety, instinctive behaviours, decrease of learning, memory, locomotor activity, curiosity, attention and/or sensory perception.

The present invention is also related to a transgenic non human animal which comprises the nucleic acid molecule according to the invention or the vector according to the invention. Said vector adapted for expression in a cell or in a transgenic non human animal is any molecule or microorganism which may transfect said cell or said animal and may express in said cell or said animal the exogenous nucleic acid molecules it comprises. Said vector may be a plasmid, a recombinant virus, a baculovirus, an adenovirus, . . . .

Another aspect of the present invention of the present invention is related to a method for recovering an inhibitor net known to be capable of specifically binding to the peptide according to the invention can specifically bind to it; said method comprises contacting the peptide according to the invention under conditions permitting binding of an inhibitor known to bind the peptide according to the invention, determining the presence of any inhibitor bound to said peptide and recovering said inhibitor.

The present invention is also related to a method for recovering a compound not known to be capable of specifically binding as an antagonist or as an agonist of the peptide according to the invention, specifically the peptide of an $ORL_1$ receptor, preferably a mammal $ORL_1$ receptor, specifically a human $ORL_1$ receptor, can specifically bind to said receptor; said method comprises contacting a cell, preferably a mammalian cell, comprising the vector adapted for expression in a mammalian cell, which vector further comprises nucleic acid molecules which express said $ORL_1$ receptor on the cell surface with the compound under conditions permitting biding of the peptide known to bond to said receptor, and detecting the presence of any compound bound to said receptor and recovering said compound.

According to another embodiment of the present invention, said method comprises preparing a cell extract from a cell, preferably a mammalian cell, which comprises a vector adapted for expression in said cell, said vector further comprises nucleic acid molecules which express the receptor of the peptide according to the invention on the cell surface, isolating a membrane fraction from the cell extract, incubating the compound with the membrane fraction under conditions permitting the binding of the peptide known to bind to said receptor and detecting the presence of any bound compound and recovering said compound.

The present invention concerns also a method for recovering a compound not known to be capable of binding as an antagonist or as an agonist of the peptide according to the invention to a $ORL_1$ receptor, preferably a mammal $ORL_1$ receptor, more specifically a human $ORL_1$ receptor, and prevent the peptide according to the invention to activate said receptor, which comprises contacting a cell, preferably a mammalian cell, which cell comprises a vector adapted for expression of said cell, such vector further comprising nucleic acid molecules which express said receptor on the cell surface with the compound under conditions permitting measure of a functional response, determining whether the compound prevents the peptide to activate said receptor, and recovering said compound.

According to said method, the cell is a non neuronal cell comprising the cellular components necessary to produce a second messenger and wherein the determination (of whether the compound blocks the activation of the $ORL_1$ receptor by a peptide according to the invention or mimics inactivation of the $ORL_1$ receptor by a peptide according to the invention) comprises means for detecting the changes in the concentration of the second messenger, which is preferably chosen among the group consisting of cyclic AMP, inositol phosphate metabolite or intracellular calcium the modification of said second messenger is preferably monitored by a secondary production of a report molecule (such as a luciferase, a β-galactosidase, a chloramphenicol acetyltransferase, a grove hormone, . . . ) or by the physiological modification of the cell preferably monitored by measure of the extra-cellular pH.

Preferably, the non neuronal cell used in the method according to the invention is CHO.

The present invention concerns also the compound identified by the method according to the invention and the pharmaceutical composition comprising said compound and a pharmaceutically acceptable carrier.

The present invention concerns also the diagnostic and/or dosage device which comprises the inhibitor, the peptide and possibly their receptor(s), preferably the $ORL_1$ receptor according to the invention.

A last aspect of the present invention is a method of genetic treatment or prevention of a disease induced by the peptide or the nucleic acid sequence according to the invention in an animal, specifically in a human, wherein an inhibitor or a nucleic acid molecule encoding said inhibitor is administered to a patient with a pharmaceutically acceptable carrier to reduce the expression and/or the "effects" resulting from expression of said peptide or said nucleic acid sequence.

SHORT DESCRIPTION OF THE DRAWINGS

The FIG. 1 represents the effects of repeated i.c.v. injections of mouse antisense mAS or of human missense hAS oligodeoxynucleotide on the latencies to rearing and escape jumping of mice in the hot plate test of Eddy and Leimbach [11].

The FIG. 2 represents the inhibition by etorphin of forskolin (FSK)-induced accumulation of cAMP in CHO ($ORL_1^+$), a recombinant CHO cell line stably expressing orphan receptor $ORL_1$.

The FIG. 3 represents the purification of endogenous ligand of the orphan receptor $ORL_1$.

The FIG. 4 represents the inhibition by the synthetic heptadecapeptide (s-HpDPep) and its $^1$Tyr analog of forskolin-induced accumulation of cAMP in recombinant CHO ($ORL_1^+$) cells.

The FIG. 5 represents the effects of a single i.c.v. injection of the synthetic heptadecapeptide (s-HpDPep) on the latencies to rearing and escape jumping of mice in the hole plate assay [11].

The FIG. 6 represents the comparison of the sequences of the endogenous heptadecapeptide referred to here as $ORL_1$-HpDPep (SEQ ID NO: 2), and of dynorphin (SEQ ID NO: 5). The sequence of the dynorphin is that of porcine pituitary dynorphin $A^9$.

The FIG. 7 represents the general organisation of pre-pronociceptin (PPNOC gene) and a comparison between the translated regions of the human prepronociceptin (hPP-NOC)-enkephalin (hPPENK), dynorphin (hPPDYN) and opioimelanocortin (hPPOMC) genes.

The FIG. 8 represents the tissue specific expression of rat prepronociceptin mRNA by Northern blot analyses.

The FIG. 9 represents the human chromosome 8 and the physical map of its short arm in the neighbourhood of the prepronociceptin gene (PPNOC).

The FIG. 10 represents the effects of increasing doses of nociceptin on horizontal locomotor activity in mice.

The FIG. 11 represents the effects of naloxone on nociceptin-induced stimulation of horizontal locomotor activity in mice.

The FIG. 12 represents the effects of increasing doses of SCH 23390 on nociceptin-induced stimulation of horizontal locomotor activity in mice.

The FIG. 13 represents the effects of increasing doses of haloperidol on nociceptin-induced stimulation of horizontal locomotor activity in mice.

DESCRIPTION OF THE INVENTION

1. Ligand of the $ORL_1$ Receptor

The ORL1 receptor is an orphan receptor whose human [1] and murine [2–8] cDNAs have been recently characterized. $ORL_1$ (Opioid Receptor-Like 1) is structurally akin to opioid receptors and has been shown to be negatively coupled with adenylate cyclase [1]. $ORL_1$ transcripts are abundant in a number of brain regions [6, 18, 20] such as the central nervous system, especially in limbic areas, hypothalamus, pons and spinal cord, suggesting that the $ORL_1$ receptor may regulate a number of central processes including learning and memory, attention and emotions, homeostasis and sensory perception.

The Inventors describe hereafter the isolation of a peptide according to the invention, which is a ligand of the ORL1 receptor. Said naturally occurring ligand was purified on the basis of its anticipated ability to inhibit forskolin-induced cAMP accumulation in stable recombinant CHO(ORL1+) but not in non recombinant CHO(ORL1−) cells. The ligand is a novel neuropeptide which resembles the endorphin dynorphin A [9, 19] and whose amino acid sequence is F-G-G-F T-G-A-R-K-S-A-R-K-L-A-N-Q (SEQ ID NO: 2). Two other peptides were also isolated. Their amino acid sequences are: F-S-E-F-M-R-Q-Y-L-V-L-S-M-Q-S-S-Q (SEQ ID NO: 3) and T-L-H-Q-N-G-N-V (SEQ ID NO: 4). The first synthetic heptadecapeptide inhibits adenylate cyclase with an $IC^{50}$ 1 nM in CHO(ORL1+) cells in culture and, when administered in vivo, induces hyperalgesia in mice. The latter effect is consistent with the observation that in vivo inhibition of ORL1 expression with an antisense oligonucleotide induces hypoalgesia in these animals. Taken together, our data support the notion that the first discovered heptadecapeptide is a potent ORL1 receptor agonist and that it is endowed with pronociceptive properties. The second discovered heptadecapeptide presents also pronociceptive properties.

Comparison of the primary structures of $ORL_1$ and of mu-, delta- and kappa-opioid receptors revealed numerous amino acid identities, not only in the putative transmembrane domains but also in the four putative cytoplasmic loops. Although $ORL_1$ does not resemble more one subtype of opioid receptor than the two others, it displays many acidic amino acid residues in its second exofacial loop, a trait that singles the kappa out of opioid receptor types. The orphan receptor, $ORL_1$, mediates inhibition of forskolin-induced accumulation of cAMP by the opiate etorphine in a recombinant etorphine is 2 to 3 orders of magnitude less potent in inhibiting the cyclase via the $ORL_1$ than via an opioid receptor.

Figure 1:
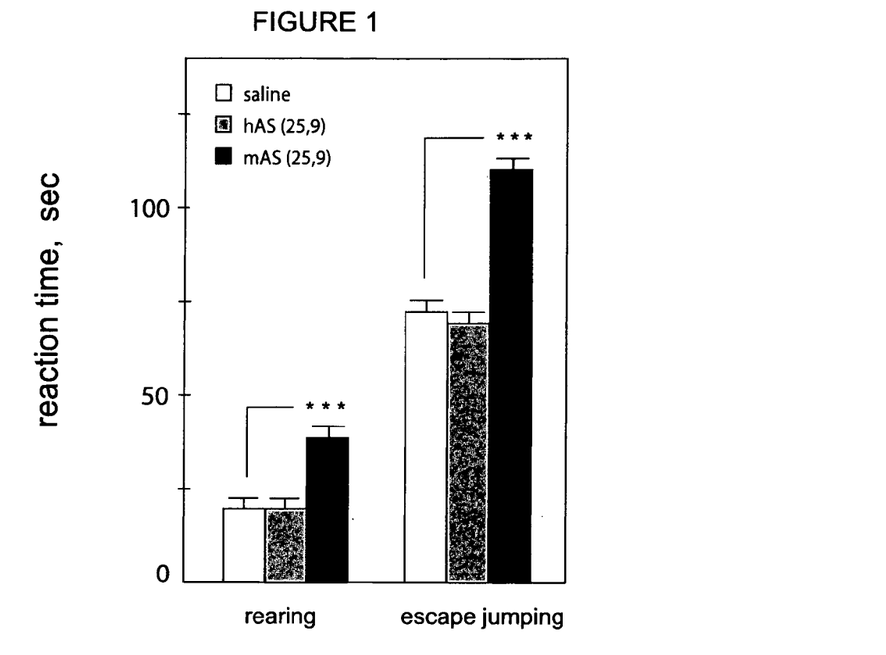

The Inventors have obtained evidence for a possible involvement of $ORL_1$ in the perception of pain. The strategy used was that of the antisense oligonucleotide [10] to inhibit expression of the $ORL_1$ receptor. Repeated in vivo treatment with an antisense oligonucleotide to $ORL_1$ mRNA rendered mice less reactive to thermal nociceptive stimulation. FIG. 1 shows that, in the hot plate assay of Eddy and Leimbach [11], the animals which had been treated with antisense oligonucleotide mAS[25,9] displayed substantially increased latencies to rearing and escape jumping in comparison with saline-treated animals: 38±2 ($p<0.001$) vs 20±2 sec and 108±6 ($p<0.001$) vs 71±6 sec, respectively. Most significantly, the "missense" oligonucleotide hAS[25,9], the human counterpart of mAS[25,9], was totally ineffective in this respect, indicating that the hypoalgesic effects elicited by the antisense mAS[25,9] were not due to non specific actions. Since a treatment with the antisense oligonucleotide should have decreased expression of the receptor, it could be predicted that $ORL_1$ normally facilitates pain perception.

Owing to the potential importance of this notion in neurophysiology and, possibly, neurophysiopathology, identification of an endogenous ligand of the $ORL_1$ receptor had become a major issue.

Figure 2:
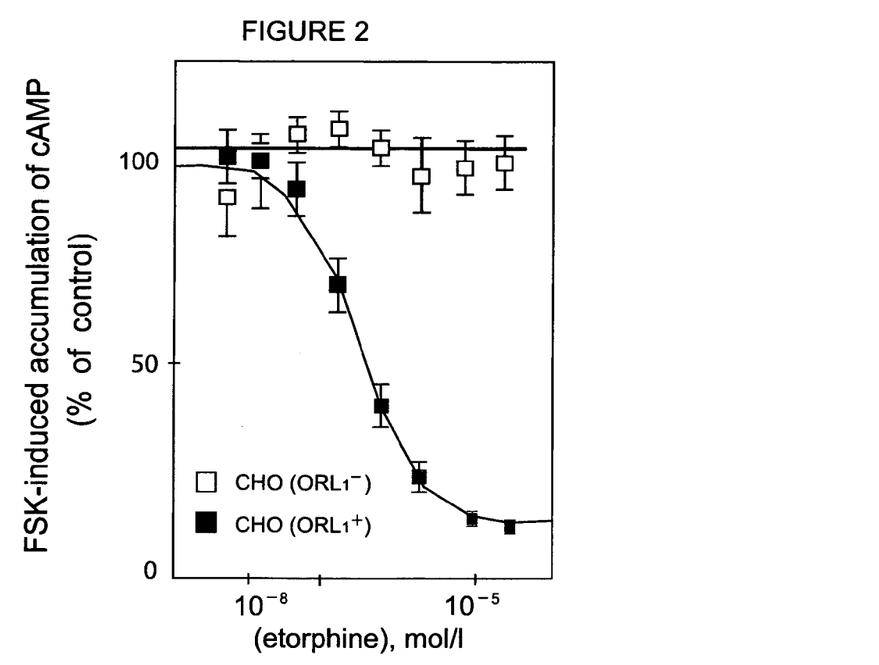

The strategy for isolating an endogenous ligand of ORL1 was based on the fact that the orphan receptor is negatively coupled with adenylate cyclase. The desired compound was therefore expected to inhibit forskolin-induced accumulation of cAMP in the recombinant $CHO(ORL_1^+)$ but not in the non recombinant $CHO(ORL_1^-)$ cell line, as previously shown for etorphine (FIG. 2). The choice of the initial extraction procedure from rat brain was largely based on the structural homology of $ORL_1$ with opioid receptors in general and the kappa receptor in particular. Extracellular loop 2 of the kappa-opioid receptor is required for high affinity binding of dynorphins [12, 13]. Since $ORL_1$ possesses such an acidic second exofacial loop, the ligand in question might be a peptide which resembled dynorphin. Therefore, we used the extraction procedure that allowed Teschemacher et al. to isolate a pituitary peptide that was later identified as dynorphin A [9].

Figure 3A:
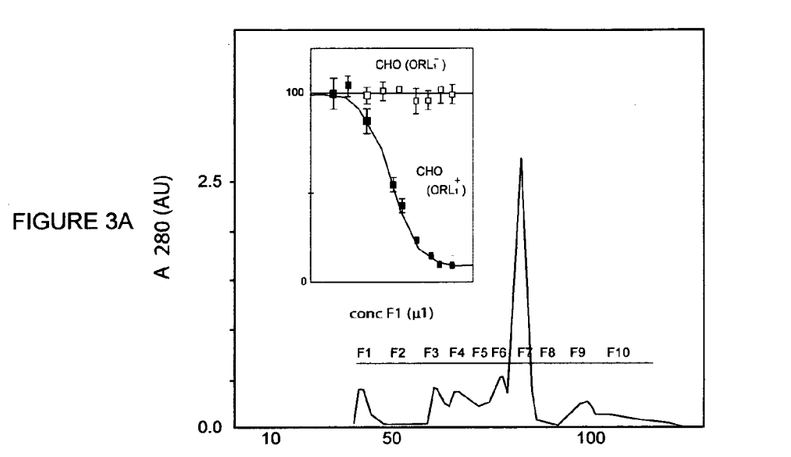
Figure 3B:
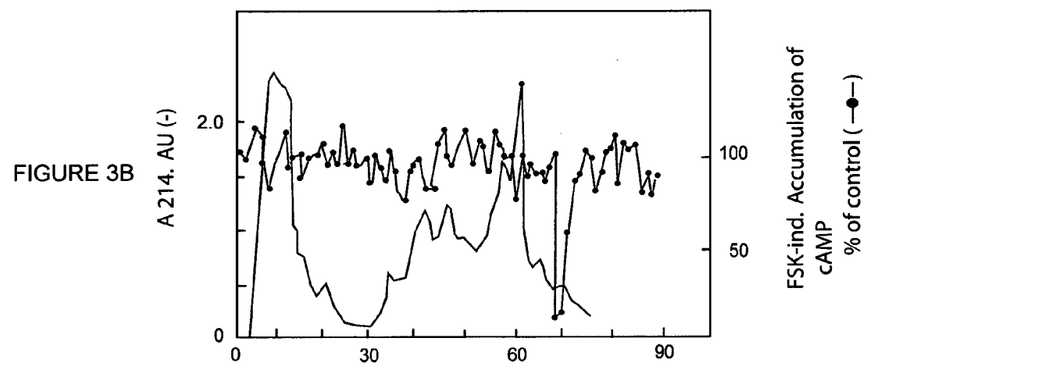
Figure 3C:
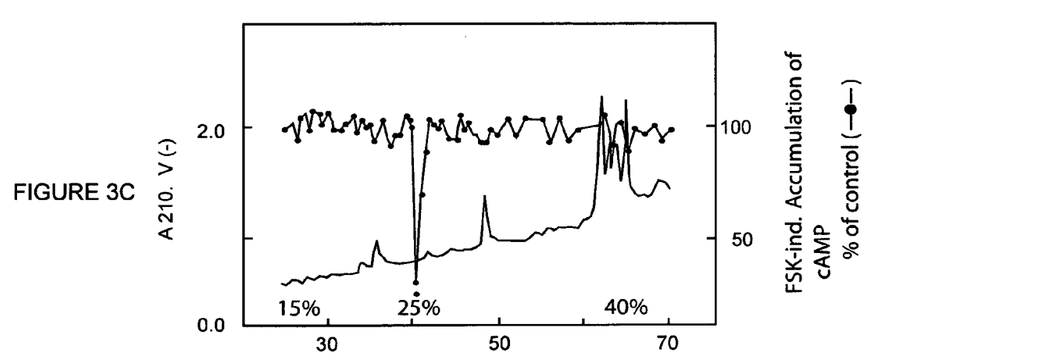

The first purification step, size exclusion chromatography of the crude peptide extract on Bio-Gel P-2, proved efficient in revealing the desired activity, i.e. inhibition of cAMP accumulation in $CHO(ORL_1^+)$ but not in $CHO(ORL_1^-)$ cells (FIG. 3a). The active fractions were recovered in the void volume (pool F1) and, to some extent in pool F2 (not shown), indicating that the biologically active substance had a $M_r$ around 1,800, the nominal exclusion limit of Bio-Gel P-2. Pools F3 to F10 were either inactive or equally effective in inhibiting (or stimulating in the case of F7) adenylate cyclase in the two CHO cell lines (data not shown). Pool F1 was further purified by cation exchange FPLC (FIG. 3b). Activity was recovered in two consecutive 1-ml fractions eluted at nearly 0.4 M NaCl, indicating the strongly basic nature of the active compound(s). These two fractions were then applied directly onto a reversed phase HPLC column and gradient-eluted with acetonitrile (FIG. 3c) to yield enough material of sufficient purity for protein sequencing. This material was found to be a heptadecapeptide of average molecular mass 1,810 and whose sequence was determined to be Phe-Gly-Gly-Phe-Thr-Gly-Ala-Arg-Lys-Ser-Ala-Arg-Lys-Leu-Ala-Asn-Gln (SEQ ID NO: 2).

Figure 4:
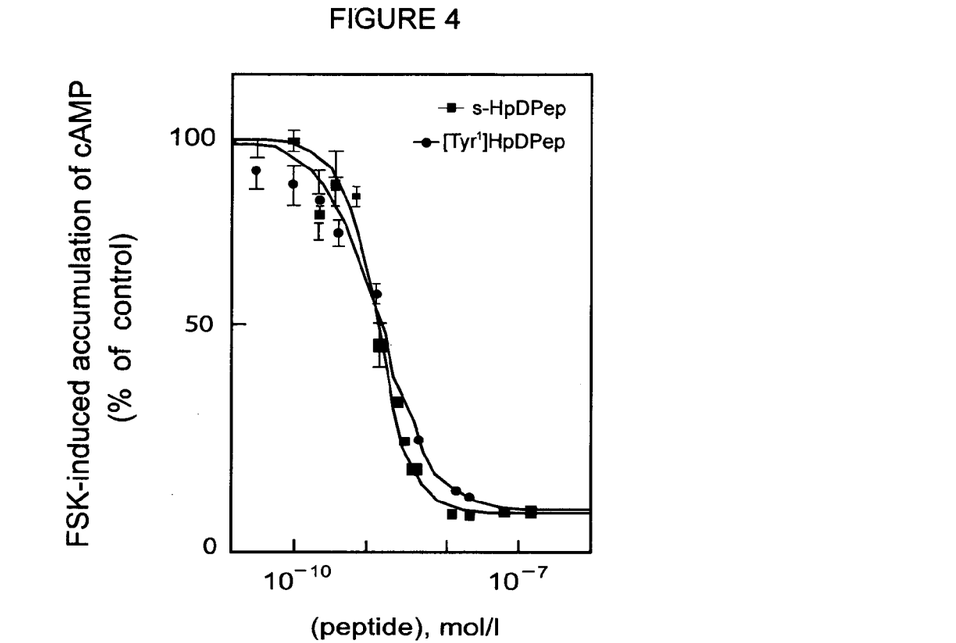

To make sure that the sequence in question was not that of a major contaminant, the heptadecapeptide was synthetized as well as its $^1$Tyr analogue for the purpose of generating a radioiodinated probe. The two peptides were obtained at $\geq$98% purity as assessed by RP-HPLC and had the predicted molecular masses (1,809 and 1,825 respectively) as assessed by mass spectrometry. FIG. 4 shows that the synthetic heptadecapeptide was very potent in inhibiting forskolin-induced accumulation of cAMP in the recombinant CHO(ORL$_1^+$) cell line. Its IC$_{50}$ was 0.9×10$^{-9}$ mol/l and maximal inhibition amounted to 90%. The synthetic peptide had no action on cyclase in the non recombinant CHO (ORL$_1^-$) cell line at concentration up to 1 µM. Interestingly, the $^1$Tyr analogue was as effective as the parent peptide on cyclase in CHO cells expressing the receptor (IC$^{50}$=1.0× 10$^{-9}$ mol/l, maximal inhibition>90%) and totally inactive in the wild type cells.

Figure 5:
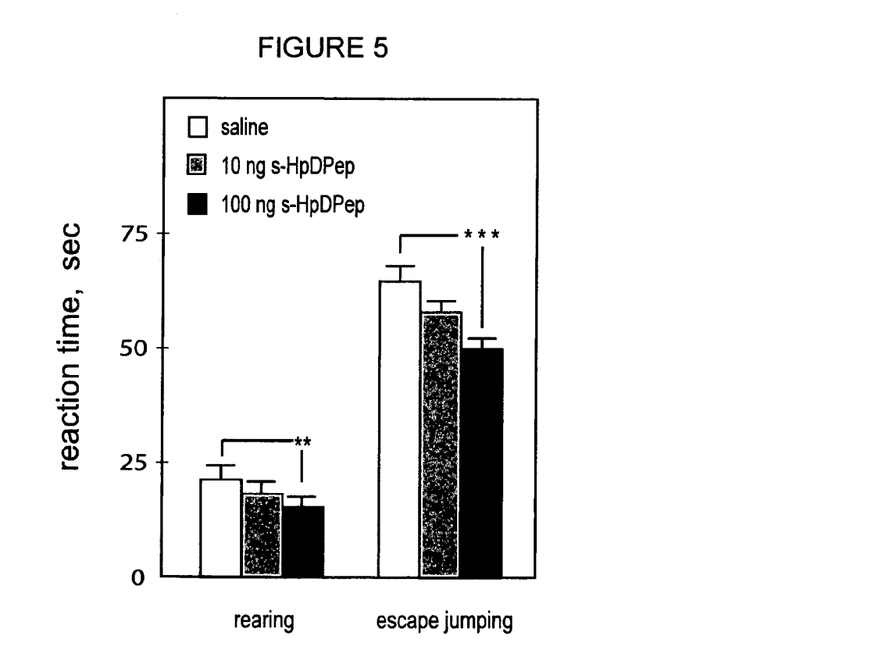

The synthetic heptadecapeptide was also found to be active in vivo. Intracerebroventricular injection of 10 or 100 ng of the peptide rendered mice hyperreactive in the hot plate test [11]. FIG. 5 shows that the hyperalgesic effect was dose dependent for 10 ng (5.5 pmol) and 100 ng (55 pmol) of peptide. A highly significant reduction of the latencies to rearing and escape jumping was observed at the larger dose of peptide: 14±2 (−36%, p<0.01) vs 22±2 and 48±2 (−26%, p<0.001) vs 65±3 sec, respectively. These effects were exactly the opposite of those produced by in vivo inhibition of expression of the ORL$_1$ receptor (FIG. 1).

Figure 6:
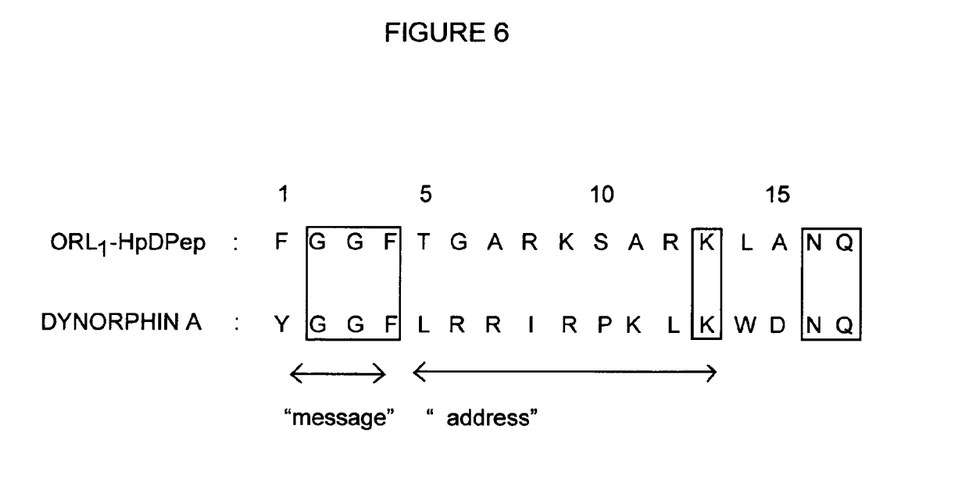

The heptadecapeptide sequence did not exist in data banks although it was found to bear some resemblance with those of dynorphins, especially dynorphin A (FIG. 6). The structural homologies between this novel peptide and dynorphin A support the idea that the former may interact with the ORL1 receptor as the latter does with the kappaopioid receptor [12, 13, 15]. In particular, the novel peptide may be viewed as made up of a N-terminal Phe-Gly-Gly-Phe (residues 1–4 of SEQ ID NO: 2) "message" for biological activity, followed by a Thr-Gly-Ala-Arg-Lys-Ser-Ala-Arg-Lys (residues 5–13 of SEQ ID NO: 2) "address", for enhanced potency[15]. The "address" contains all the basic amino acid residues that are anticipated to bind the acidic second exofacial loop of the ORL1 receptor.

The sequence of the endogenous ligand of ORL1 is likely to be highly conserved across species. Indeed, the Inventors have also isolated a bovine brain peptide with the same biological activity and the same molecular mass (1,810 ±2) as the rat peptide. There was not enough of this peptide for complete sequencing, but 10 residues could be determined (4–8, 11, 12 and 14–16) that were identical to the corresponding amino acids in the rat sequence.

Several investigators have pointed out that the ORL$_1$ receptor might play a crucial role in pain perception [1, 4] and locomotion/curiosity control. Two in vivo observations now give experimental support to this notion:
(i) inhibition of receptor expression with an antisense oligonucleotide induces hypoalgesia (FIG. 1), and
(ii) intracerebroventricular administration of the heptadecapeptide induces hyperalgesia (FIG. 5), in mice.

Thus, the neuropeptide is endowed with pronociceptive properties and we suggest that it might be named nociceptin. Together, nociceptin and its receptor, ORL$_1$, may represent the molecular basis to a novel pain regulatory modality in the central nervous system.

Finally, the striking structural homologies which exist between the ORL1 and opioid receptors and between the novel peptide and endorphins, make it likely that the genes encoding the two classes of receptors and those encoding the two classes of neuropeptides have evolved in parallel, each from a common ancestor. Since dynorphin A is one of several prodynorphin[16]-derived endorphins, one may anticipate that the novel peptide is but one representative of a larger family whose other members await identification.

As the ORL$_1$ is located in specific parts of the brain, such as the central nervous system, especially in limbic areas, hypothalamus, pons and spinal cord, said receptor and its ligand may be involved in the control of other functions and related behaviours. For instance, the ORL$_1$ receptor and its ligand may regulate neuroendocrine secretion, stress, learning and memory, attention and emotions, homeostasis and sensory perception, motricity (locomotion), anxiety, instinctive behaviour, curiosity, . . . .

Thus, the present invention is also related to any molecule which may affect said functions and behaviours and which is a ligand of the ORL$_1$ receptor.

2. Comparative Organisation of the Prepronociceptin (PP-NOC) and Opioid Peptides Precursor Genes The present invention is also related to the nucleic acid sequence having more than 70% homology with the nucleic acid sequence SEQ ID NO. 1 which encodes the peptide according to the invention.

Such a peptide is the prepronociceptin which may be cleaved into the two heptadecapeptides according to the invention.

Figure 7:
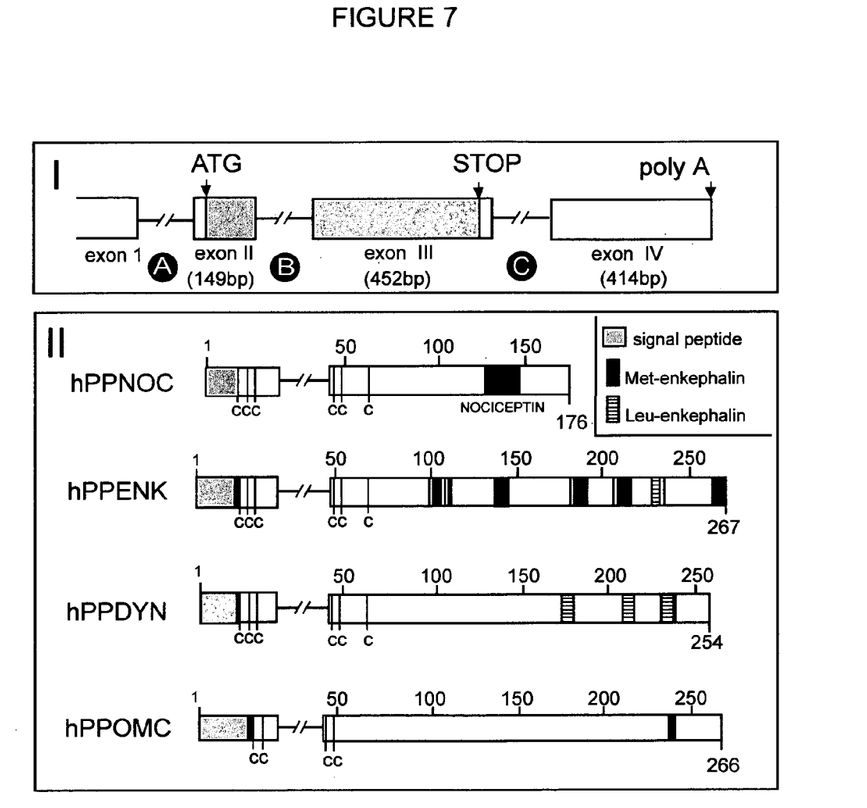

The FIG. 7 (upper panel) shows the general organisation of the prepronociceptin (PPMOC) genes. The PPMOC genes consist of 4 hexons (number I to IV) interspersed by 3 introns (A, B and C). The filled boxes correspond to the coding region. ATG, STOP and poly A are respectively the transcription start, stop and poly-adenylation sites.

The nucleotide sequence of the murine and human prepronociceptine (PPNOC) genes displays organizational and structural features which are very similar to those genes encoding the precursors to endogenous opioid peptides, enkephalins (PPENK), dynorphins/neo-endorphins (PPDYN) and β-endorphin (PPOMC) (FIG. 7, lower panel). In particular, the translated region of the murine and human PPNOC genes is interrupted by an intron located between codons for amino acids 42 et 43. An intron is also present at the equivalent site in the PPENK, PPDYN and PPOMC genes. As it is the case in opioid peptide genes, another intron is also present in the 5' untranslated region of the PPNOC gene. In addition to these two introns shared with the other precursor genes, the PPNOC gene also includes an intron in the 3' untranslated region of the message, which is unusual. Nevertheless, the present data are compatible with the notion that the nociceptin and opioid peptides genes have evolved in parallel from a common ancestor.

The deduced amino acid sequence of prepronociceptin is highly conserved across murine and human species, especially the C-terminal quarter which hosts nociceptin itself. The N-terminal end of the precursor consists of a hydrophobic stretch of about 20 amino acids which may represent the signal peptide necessary for translocation into the rough endoplasmic reticulum, followed by a cystein-rich portion which is also found in other hormone precursors, especially those to endogenous opioid peptides. Indeed, the pattern of cystein residues in pronociceptin is exactly the same as in proenkephalin and prodynorphin, suggesting a common mode of folding and/or processing of these precursor proteins. Lowest homology across murine and human prepronociceptins is observed in the core of the molecule with insertion of a variable number of repeated acidic motifs. The unique nociceptin sequence is located in the C-terminal fourth of the precursor where it is flanked by canonic Lys-Arg proteolytic excision motifs. Interestingly, pronociceptin contains other potential cleavage sites: one, Lys-Arg in the murine or Arg-Arg in the human sequence, is located upstream, and the other, Arg-Arg-Arg, downstream of nociceptin. Pronociceptin may therefore serve as the precursor not only to the two identified heptadecapeptides and the octapeptides but also to other physiologically important (neuro)peptides according to the invention.

3. Tissue Distribution of rat Prepronociceptin mRNAs

Figure 8:
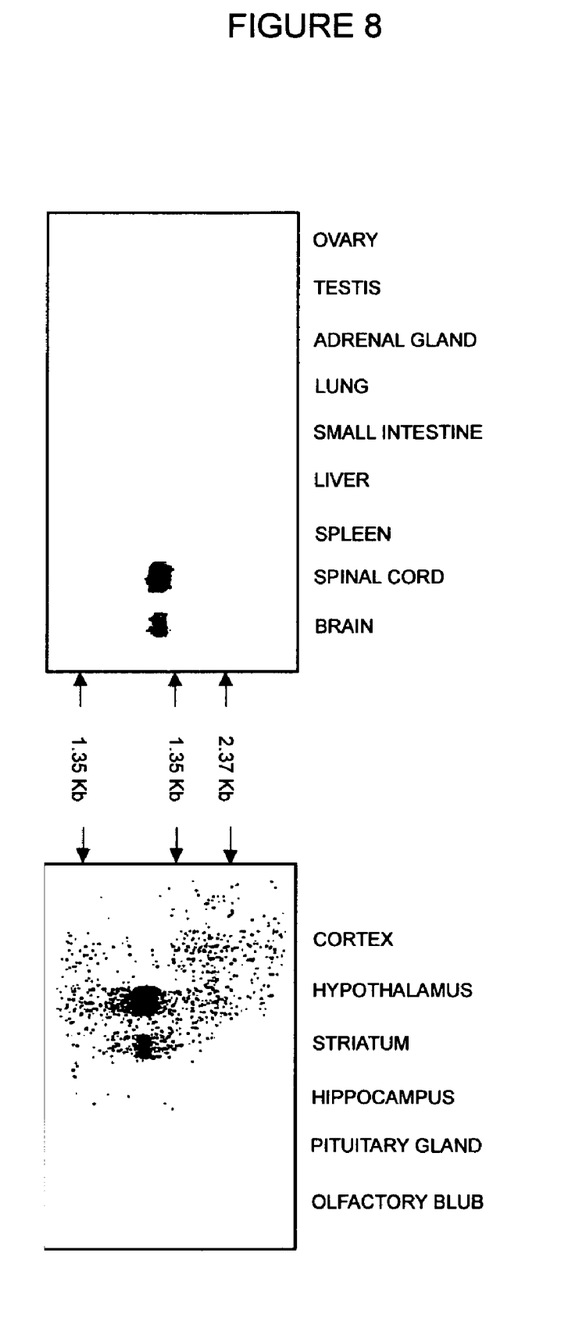

Northern blot analysis (FIG. 8) revealed that prepronociceptin messenger RNAs are present as a single species about 1.3 kb long in rat nerve tissue (brain and spinal cord) as well as in ovary. No signal could be detected in RNA extracts from peripheral tissues, including liver, intestine, stomach, lung, spleen, adrenal gland and testis.

4. Mapping of the Human Prepronociceptin Gene

Figure 9:
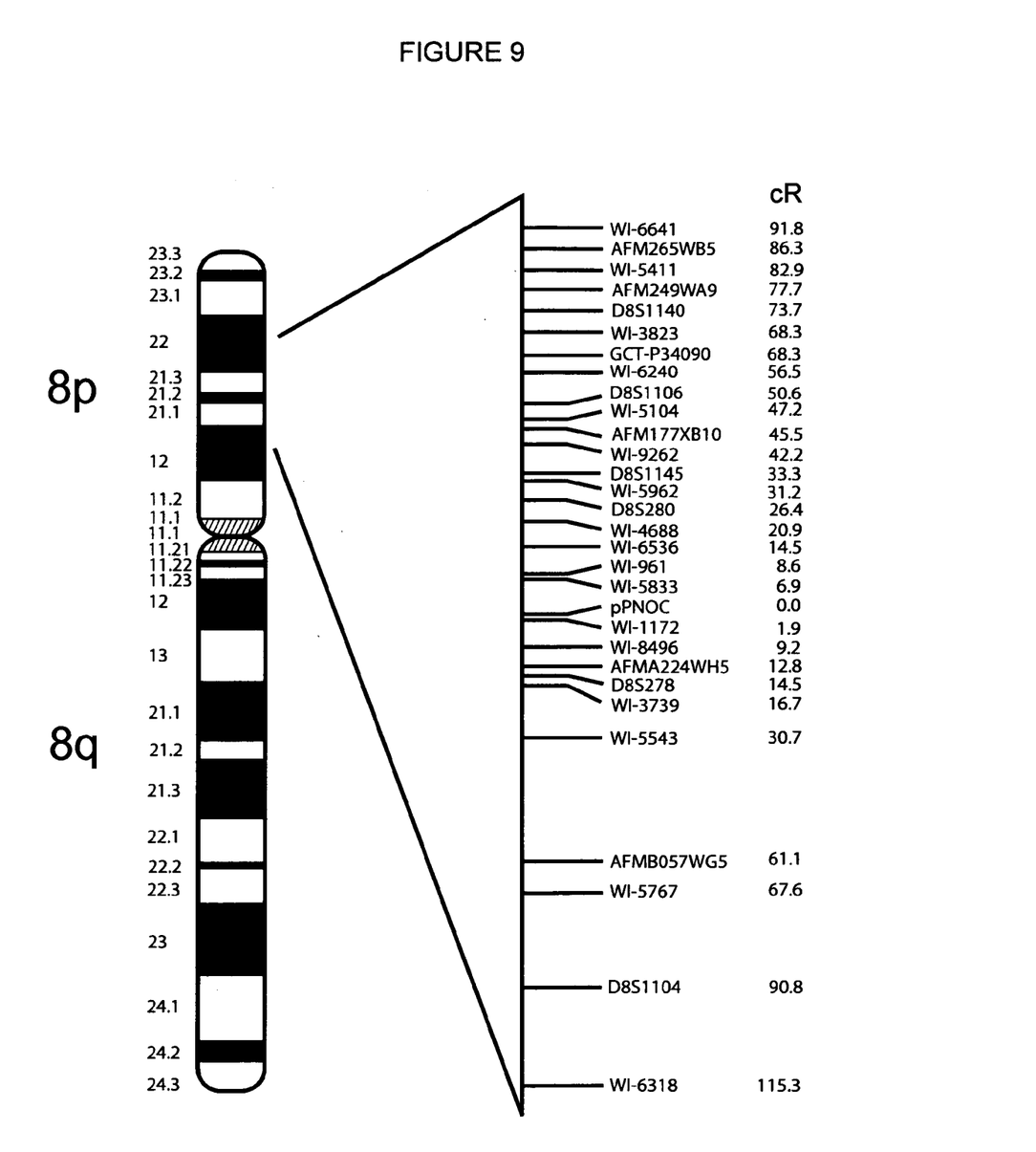

The human prepronociceptin gene was mapped by performing polymerase chain reactions on the radiation hybrid cell lines of the GeneBridge 4 panel. The Rhmapper program allowed to assigned unambiguously the gene to human chromosome 8, between the STS markers WI-5833 and WI-1172 (FIG. 9).

5. Stimulation of Locomotion and Curiosity by Nociceptin in Mice

Early behavioral and functional studies indicated that the nociceptin peptide might exert awakening and psychostimulant actions in mice. The results confirm the preliminary observations by examining the effects of nociceptin on the horizontal and vertical components of locomotion as well as on exploratory behaviour. Since the $ORL_1$ receptor resembles opioids receptors and nociceptin dynorphin A, it has been verified that nociceptin-induced stimulation of locomotion in mice is insensitive to the opioate antagonist naloxone [22] and the locomotor effects of the peptide involve, as expected, dopamine transmission.

Material and Methods

Animals

Male Swiss albino mice (CD1, Charles River, Saint Aubin lès Elbeuf, France) weighting 20–25 g were used in this study. They were housed 20 per box (L: 40 cm, W: 25 cm, H: 18 cm), with unlimited access to standard semi-synthetic laboratory food and tap water, under controlled environmental conditions (temperature: 22±1° C., 7 a.m. to 7 p.m. light-dark cycle). Experiments were carried out between 10 a.m. and 6 p.m. Each animal was used once.

Intracerebroventricular Infections

Injections (10 µl) were performed free hand in the left ventricle [23]. The animals were routinely tested from the 5th minute after injection.

Locomotor Activity

Locomotor activity was assessed using a Digiscan Animal Activity Monitor (Omnitek Electronics Inc.) This system consists of cages (L: 20 cm, W: 20 cm, H: 30 cm) surrounded by two surimposed sets each of 8 IR beam sensors, the lower set for monitoring horizontal and the upper, vertical deplacements, and interfaced with an Apple IIe computer. The cages were placed in dimly lit, sound-attenuated room.

Hole Board Test

The hole board test [24] consists in a plastic square plate (20×20 cm, 1 cm thick) with 16 holes, 2 cm in diameter, evenly spaced at 3.5 cm from the edges. The animals were placed in the centre of the plate and the number of head dips was measured during 4 consecutive periods of 5 minutes each.

Drugs and Solutions

The nociceptin peptide according to the invention was solid phase synthesised. Naloxone hydrochloride was from Endo and SCH 23390® [25] from Schering. Haloperidol [26] solutions were obtained by dilution in saline (NaCl 0.9% w:v) of Haldol® (Janssen).

Statistical Analyses

The data are expressed as the mean±standard error. Differences between groups were assessed by two-ways analysis of variance (ANOVA) and the Student's t-test. $P<0.05$ was taken as the significant level of difference.

Results

Figure 10:
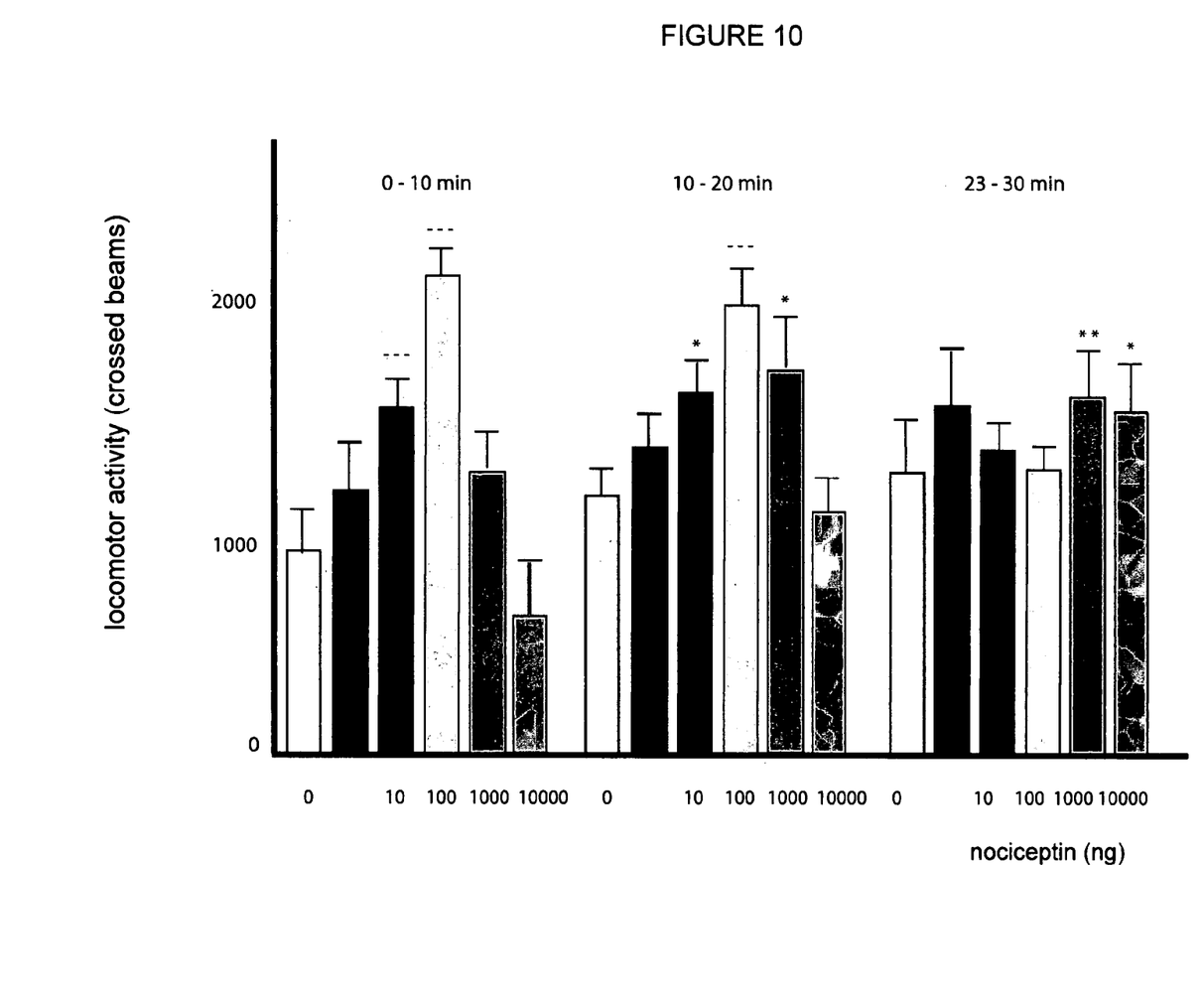

The FIG. 10 shows that i.c.v. injection of a dose of nociceptin at low 10 ng/mouse elicited a statistically significant increase in horizontal locomotor activity. This effect was even more pronounced and, apparently, culminated at the dose of 100 ng. However, the stimulant action of the peptide lasted no more than 20 minutes. At higher doses (1 and 10 µg/mouse), nociceptin appeared to stimulate locomotion yet after a delay of at least 20 minutes following introduction into the monitor. The peptide also increased significantly verticalisation during the periods 0–10 and 10–20 minutes of observation at the doses of 100 ng and 1 µg. The results are expressed in the table 1.

TABLE 1

| Nociceptin doses | Number of verticalisations during periods (min) | | |
|---|---|---|---|
| (ng/mouse) | 0–10 min | 10–20 min | 20–30 min |
| 0 | 96 ± 24.3 | 131 ± 29.4 | 143 ± 33 |
| 10 | 195 ± 34 | 223 ± 39 | 222 ± 39 |
| 100 | 266 ± 41 | 253 ± 33.5 | 231 ± 34.5 |
| 1000 | 239 ± 56.2 | 301 ± 36.6 | 295 ± 50.5 |

In the hole board test, nociceptin (100 ng/mouse, i.c.v.) induced a significant increase in the number of explored holes (see table 2). During the 20 minutes period of observation, this number increased from 155±15 in saline up to 226±18 in peptide-treated animals (p<0.01). On the contrary, when the animals were injected with morphin (5 mg/kg, s.c.) and tested 15 minutes later under the same conditions as nociceptin-treated animals, the number of explored holes was considerably reduced (150±8 in saline vs 24±2 in morphin-treated group (p<0.001)).

Figure 11:
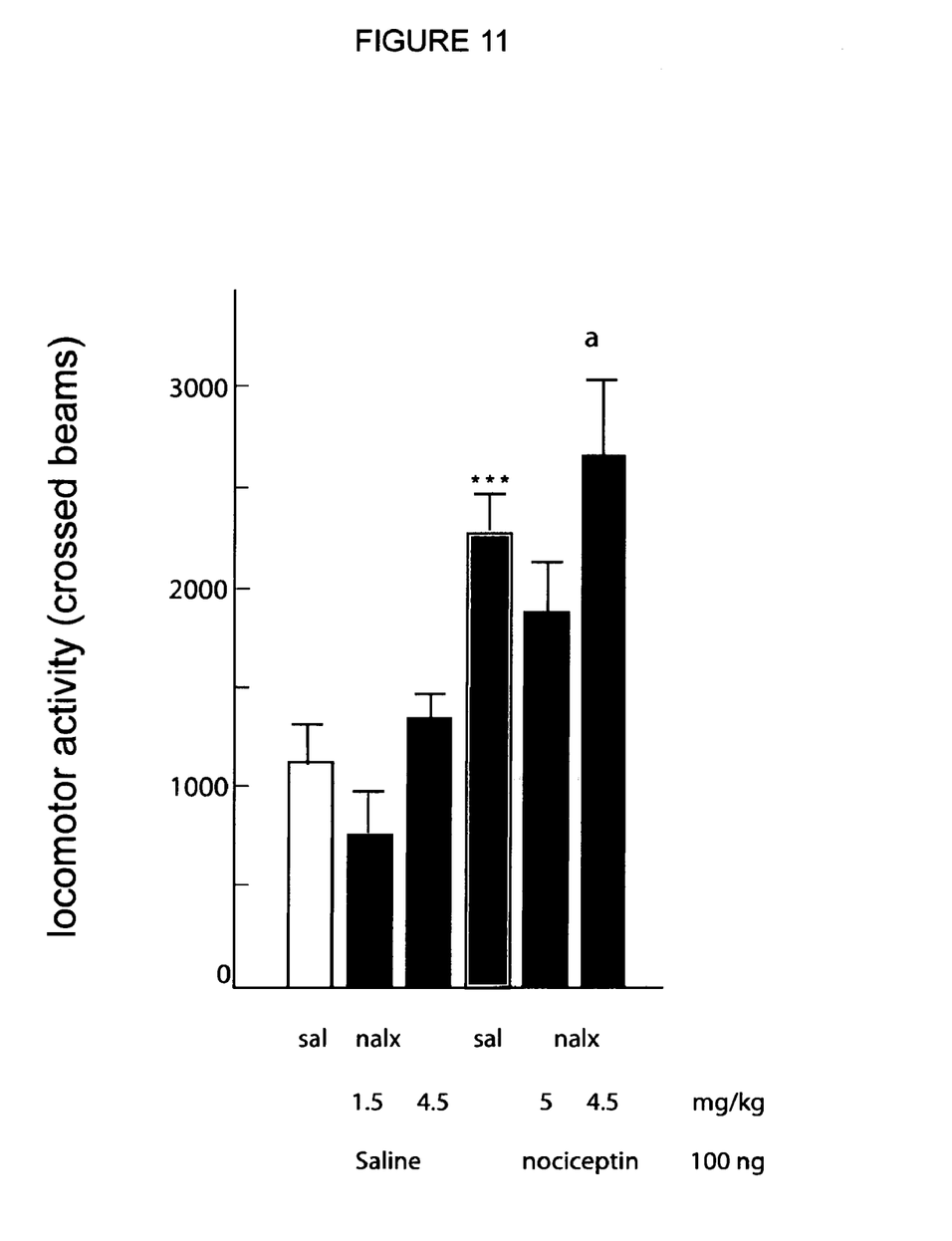

Naloxone (0.0–4.5 mg/kg, s.c.) injected 10 minutes before i.c.v. administration of 100 ng nociceptin did not suppress the motor-stimulant effect of the peptide observed during the first 10 minutes of testing (pretreatment×treatment interaction $F(1,20)=0.023$) (FIG. 11).

Figure 12:
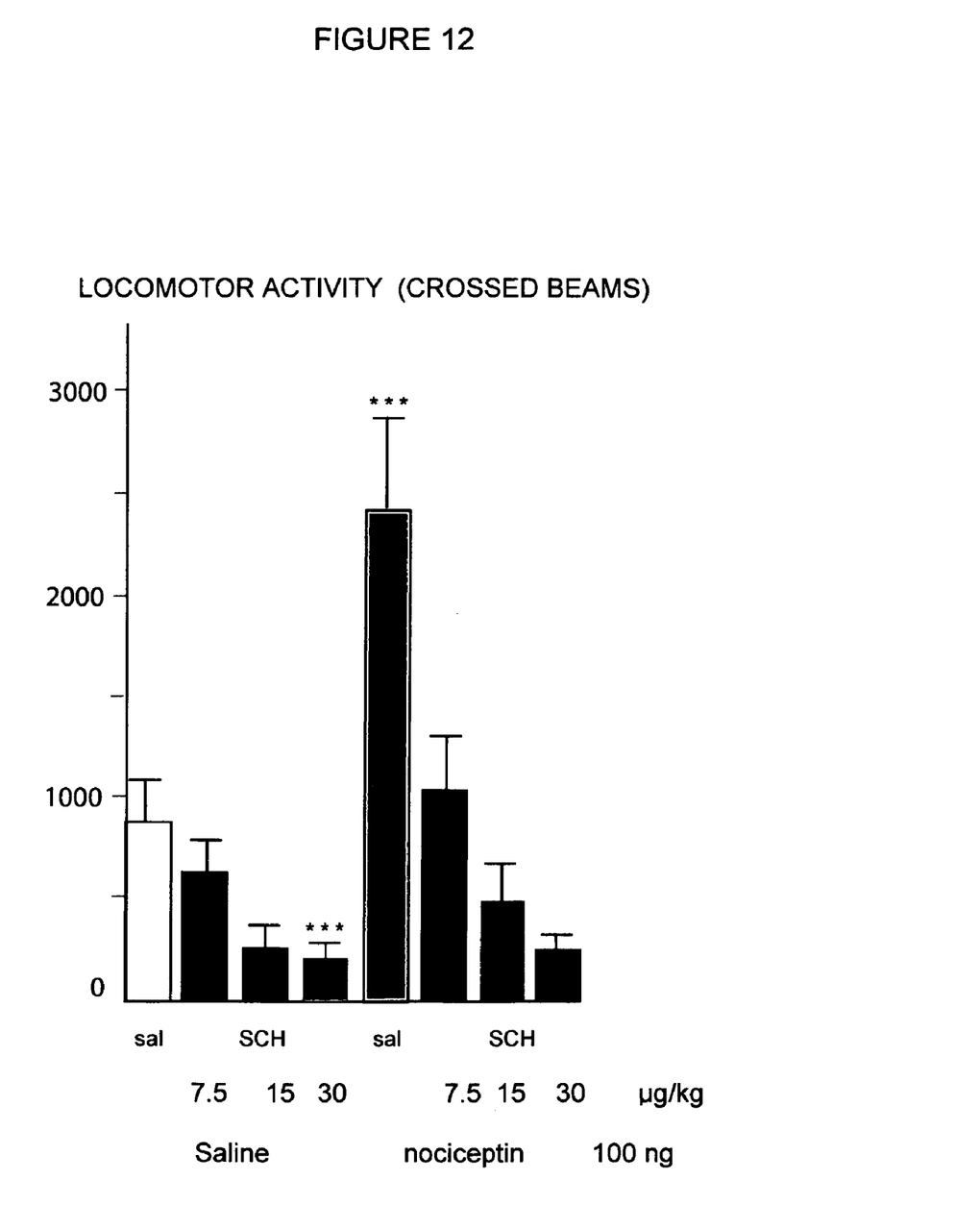
Figure 13:
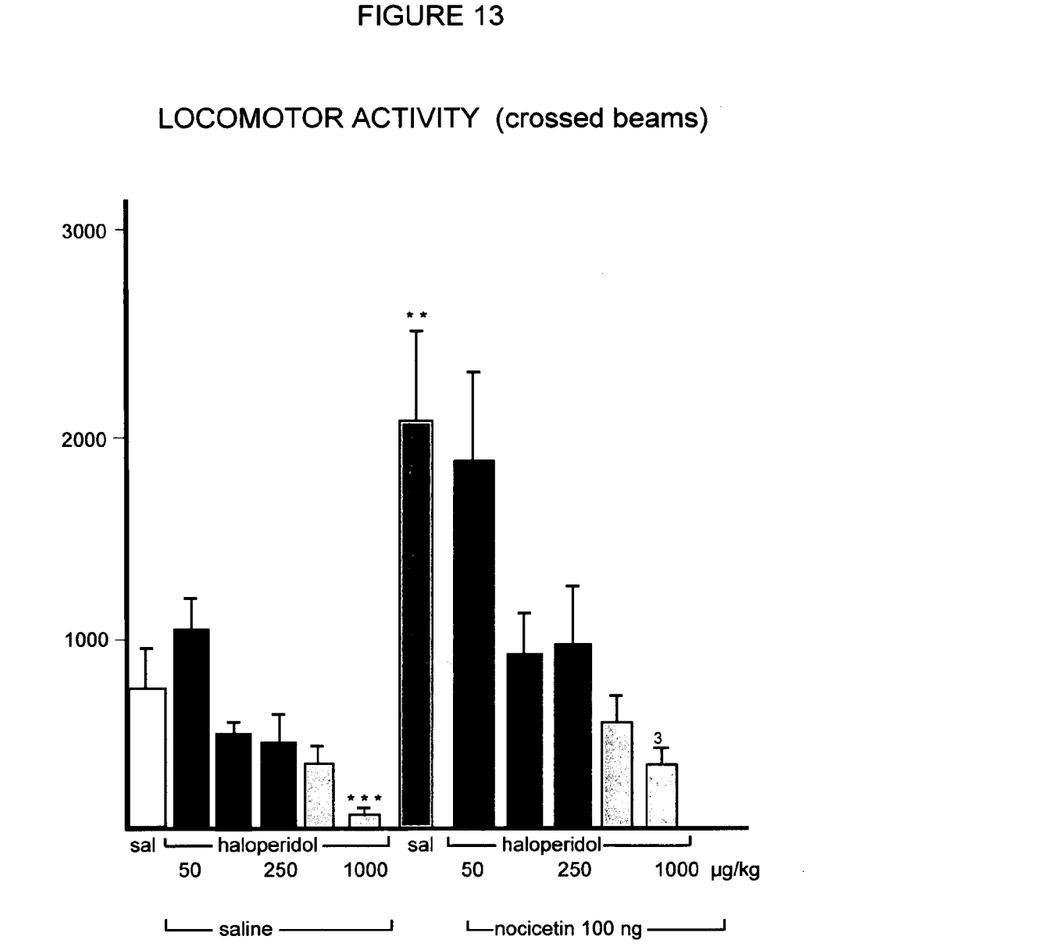

In contrast, the D1 dopamine receptor antagonist SCH 23390 proved to be effective in antagonizing nociceptin stimulation of locomotor activity in mice (pretreatment×treatment interaction $F(1,20)=4.25$ (p<0.01)) (FIG. 12). Similarly the D2 dopamine receptor antagonist haloperidol antagonized nociceptin-induces stimulation of locomotor activity (pretreatment×treatment interaction $F(1,20)=2.57$; p<0.05) (FIG. 13).

TABLE 2

| Treatments i.c.v. | Number of explored holes during the periods (min) | | | |
|---|---|---|---|---|
| | 0–5 | 5–10 | 10–15 | 15–20 |
| Saline | 28.5 ± 5.7 | 39.0 ± 4.6 | 46.8 ± 4.3 | 40.7 ± 6.5 |
| Nociceptin (100 ng/mouse) | 50.4 ± 6.8 | 64.5 ± 7.3 | 62.4 ± 5.6 | 58.6 ± 6.6 |

The neuropeptide nociceptin stimulates both the horizontal and vertical components of the locomotion in mice. This effect is already seen at the low dose of 10 ng/mouse and seems to be effective at higher dose of 100 ng/mouse. Regardless of the dose, nociceptin's action appears to be of short duration, suggesting a rapid inactivation of the peptide under the experimental conditions. At the highest dose tested (10 μg), the stimulation of horizontal locomotor activity by nociceptin does not show up until at least 25 minutes following i.c.v. injection as it is exerted, during this period, an effect opposing those of low doses of the peptide. Since it has been previously emphasized that nociceptin resembles dynorphin A, which itself and other agonists of Kappa opioid receptors depress locomotion, one could argue that such opposing action at high dose of nociceptin might follow from the aspecific stimulation of these opioid receptors.

The stimulation of locomotor activity by nociceptin does not involve opioid receptors since the peptide displays none of the properties that are characteristic of morphin. In particular, the locomotor effect which is induced by nociceptin includes a vertical component and it does not correspond to the so-called "running fit" behaviour elicited by the opiate. Neither does nociceptin induce the Straub tail phenomenon. Nociceptin is hyperalgesic in vivo and its stimulatory action on locomotion is not antagonized by the opiate antagonist naloxone.

Another large difference resides in the fact that nociceptin stimulates "curiosity" while morphin strongly decreases it. The motor-stimulant effect of nociceptin is unlikely to involve delta opioid receptor although delta opioid agonists are known to stimulate both the horizontal and vertical components of locomotion, yet this effect is reversed by naloxone and is accompanied by a naloxone-reversible analgesia in the hot plate test. Taken together, these data argue against the notion that the stimulant/awakening actions of the nociceptin in mice involve opioid receptors.

Most psychostimulant agents operate through an increase in central dopaminergic transmission. To test this hypothesis, the interaction of nociceptin with the D2 dopamine receptor antagonist haloperidol and the D1 dopamine receptor antagonist SCH 23390® was considered. Antagonism was observes in each case, indicating that dopamine neurones, likely mesolimbic ones, are involved in nociceptin-elicited stimulation of locomotion.

REFERENCES

1. Mollereau et al., F.E.B.S. Lett. 341, pp. 33–38 (1994)
2. Fukuda et al., F.E.B.S. Lett. 343, pp. 42–46 (1994)
3. Chen et al., F.E.B.S. Lett. 347, pp. 279–283 (1994)
4. Bunzow et al., F.E.B.S. Lett. 347, pp. 284–288 (1994)
5. Wang et al., F.E.B.S. Lett. 348, pp. 75–79 (1994)
6. Lachowicz et al., J. Neurochem. 64, pp. 34–40 (1995)
7. Nishi et al., Biochem. Biophys. Res. Comm. 205, pp. 1353–1357 (1994)
8. Wick et al.,. Mol. Brain Res. 27, pp. 37–44 (1995)
9. Goldstein et al., Proc. Natl. Acad. Sci. U.S.A. 78, pp. 7219–7223 (1981)
10. Wahlestedt, Trends Pharmacol. Sci. 15, pp. 42–46 (1994)
11. Eddy & Leimbach, J. Pharmacol. Exp. Ther. 107, pp. 385–393 (1953)
12. Wang et al., J. Biol. Chem. 269, pp. 25966–25969 (1994)
13. Xue et al., J. Biol. Chem. 269, pp. 30195–30199 (1994)
14. Teschemacher et al., Life Sci. 16, pp. 1771–1776 (1975)
15. Chavkin & Goldstein, Proc. Natl. Acad. Sci. U.S.A. 78, pp. 6543–6547 (1981)
16. Kakidani et al., Nature 298, pp. 245–249 (1982)
17. Alvarez & Daniels, Anal. Biochem. 203, pp. 76–82 (1992)
18. Vaughan et al., Brit. J. Pharm. 117, pp. 1609–1611 (1996)
19. Pan et al., Biochem. J. 315, pp. 11–13 (1996)
20. Sim et al., Neuropharmacology and Neurotoxicology Neuroreport 7, pp. 729–733 (1996)
21. Hudson et al., Science 270, pp. 1945–1954 (1995)
22. Sawynock et al., Life Sciences 25, p. 1621 (1979)
23. Haley et al., Brit. J. Pharmacol. 12 (1957)
24. Boisier et al., Therapy XVII, p. 1125 (1962)
25. Iorio et al., J. Pharmacol. Exp. Ther. 227, p. 462 (1983)
26. Cox et al., Brit. J. Pharmacol. 681, p. 172 (1980)

What is claimed is:

1. A method for identifying an antagonist of an opioid receptor like 1 (ORL$_1$) comprising:
   (a) contacting an ORL$_1$ receptor with a polypeptide comprising the sequence of SEQ ID NO: 2 in the presence of a candidate modulator under conditions which permit binding of said polypeptide to said ORL$_1$ receptor; and
   (b) measuring production of a second messenger wherein a change in the concentration of a second messenger measured in the presence of said candidate modulator relative to the concentration of said second messenger in the absence of said candidate modulator identifies said candidate modulator as an antagonist of said ORL$_1$ receptor.

2. The method of claim 1, wherein said second messenger is cAMP.

3. A method of identifying an agent that binds to an opioid receptor-like 1 (ORL$_1$) receptor, said method comprising:
   (a) contacting an ORL$_1$ receptor with an isolated peptide comprising the sequence of SEQ ID NO: 2 in the presence or absence of said agent under conditions permitting the binding of said isolated peptide to said ORL$_1$ receptor; and
   (b) measuring the binding of said ORL$_1$ receptor to said isolated peptide, wherein a decrease in binding in the presence of said agent, relative to the binding in the absence of said agent identifies said agent as an agent that binds to said ORL$_1$ receptor.

4. The method of claim 1 or 3, wherein said ORL$_1$ receptor is present in or on a cell.

5. The method of claim 1 or 3, wherein said ORL$_1$ receptor is present in a membrane fraction from cells which express said ORL$_1$ receptor.

* * * * *

SEQUENCE LISTING

<160> NUMBER OF SEQ ID NOS: 5

<210> SEQ ID NO 1
<211> LENGTH: 932
<212> TYPE: DNA
<213> ORGANISM: Homo sapiens

<400> SEQUENCE: 1

```
ctctccagcg tgttcagcag ctgtcccgag gactgcctca cctgccagga gaggctccac      60
ccggctccgg gcagcttcaa cctgaagctg tgcatcctcc agtgtgaaga gaaggtcttc     120
ccccgccctc tctggactct ttgcaccaaa gccatggcca gtgactctga gcagctcagc     180
```

-continued

| | |
|---|---|
| cctgctgatc cagagctcac gtccgctgct ctttaccagt cgaaagcctc ggagatgcag | 240 |
| cacctgaaga gaatgccgcg tgtcaggagt gtggtgcaag cccgagacgc agagcctgag | 300 |
| gcagatgcag agcctgtcgc agatgaggcc gatgaggtgg agcagaagca gctgcagaaa | 360 |
| aggtttgggg gcttcactgg ggcccggaag tcagcccgga agttggccaa ccagaagcgg | 420 |
| ttcagtgagt ttatgaggca gtacctggtc ctgagcatgc agtcaagcca acgccgccgc | 480 |
| actctgcacc agaatggtaa tgtgtagcca gaaggagccc ctcccagctg caccggccac | 540 |
| tgcaacccat gagcatccag gtgagccccc gtacagcatg tgtccacacc aagacctgca | 600 |
| ggccgggagt caggattcct ccttccctga ggcactgaac acccgcggca cctccccaca | 660 |
| gcatgtctca ccacaatcct gttgctacat cagagtgtat ttttgtaatt cctccagcta | 720 |
| acattttaat ggccccatct tcttgctcat cctctgccct ctcgtagggc caggtgagag | 780 |
| gaacatgaaa tcagacctgg ggttttgcct caccactgcc ataactggtt tgtaaaggag | 840 |
| ctgttctttt tgactgattg tttgaaacaa ctttctccat taaacttcta ctgagcaaaa | 900 |
| tggttaataa aaaaaaaaaa aaaaaggaat tc | 932 |

<210> SEQ ID NO 2
<211> LENGTH: 17
<212> TYPE: PRT
<213> ORGANISM: Homo sapiens

<400> SEQUENCE: 2

Phe Gly Gly Phe Thr Gly Ala Arg Lys Ser Ala Arg Lys Leu Ala Asn
1               5                   10                  15

Gln

<210> SEQ ID NO 3
<211> LENGTH: 17
<212> TYPE: PRT
<213> ORGANISM: Homo sapiens

<400> SEQUENCE: 3

Phe Ser Glu Phe Met Arg Gln Tyr Leu Val Leu Ser Met Gln Ser Ser
1               5                   10                  15

Gln

<210> SEQ ID NO 4
<211> LENGTH: 8
<212> TYPE: PRT
<213> ORGANISM: Homo sapiens

<400> SEQUENCE: 4

Thr Leu His Gln Asn Gly Asn Val
1               5

<210> SEQ ID NO 5
<211> LENGTH: 17
<212> TYPE: PRT
<213> ORGANISM: Porcine

<400> SEQUENCE: 5

Tyr Gly Gly Phe Leu Arg Arg Ile Arg Pro Lys Leu Lys Trp Asp Asn
1               5                   10                  15

Gln